US00PP34895P2

(12) United States Plant Patent
Johnson, Jr.

(10) Patent No.: US PP34,895 P2
(45) Date of Patent: Jan. 3, 2023

(54) ***BEGONIA* PLANT NAMED 'HARVEST MOON'**

(50) Latin Name: ***Begonia* hybrid**
Varietal Denomination: Harvest Moon

(71) Applicant: Ozzie W. Johnson, Jr., Marietta, GA (US)

(72) Inventor: Ozzie W. Johnson, Jr., Marietta, GA (US)

(73) Assignee: Plants Nouveau, Mobile, AL (US)

( * ) Notice: Subject to any disclaimer, the term of this patent is extended or adjusted under 35 U.S.C. 154(b) by 0 days.

(21) Appl. No.: 17/863,086

(22) Filed: Jul. 12, 2022

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./263.1, 343
See application file for complete search history.

*Primary Examiner* — Karen M Redden
(74) *Attorney, Agent, or Firm* — Cassandra Bright

(57) ABSTRACT

A new and distinct cultivar of *Begonia* plant named 'Harvest Moon' is disclosed, characterized by its distinctive foliage with a green upper surface turning copper during the Fall. Foliage underside is a warm maroon. Peduncles are long, holding most flowers above the foliage. Plants exhibit improved root hardiness and an upright plant form. Flower buds are bright pink, maturing to pink and white. The new cultivar is a *Begonia*, typically suited for garden and ornamental container use.

3 Drawing Sheets

Latin name of the genus and species: *Begonia* hybrid.
Variety denomination: 'Harvest Moon'.

BACKGROUND OF THE INVENTION

The new cultivar is a product of a planned breeding program. The new variety originated from an open-pollination of the seed parent, an unpatented, unnamed variety of *Begonia* hybrid with the pollen parent, a different *Begonia* hybrid, by the inventor during 2012. The crossing was made in Marietta, Ga. in the inventor's garden.

'Harvest Moon' was selected by the inventor, in 2013 Marietta, Ga. in the inventor's garden.

After selection of the new cultivar, asexual reproduction of 'Harvest Moon' was first performed at a hobbyist greenhouse in Alphretta, Ga. by leaf cuttings in 2014. 'Harvest Moon' has since produced several generations and has shown that the unique features of this cultivar are stable and reproduced true to type.

SUMMARY OF THE INVENTION

The cultivar 'Harvest Moon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Harvest Moon'. These characteristics in combination distinguish 'Harvest Moon' as a new and distinct *Begonia* cultivar:

1. Distinctive foliage with a green upper surface turning copper during the Fall. Foliage underside is a warm maroon.
2. Root hardiness.
3. Large leaf size.

4. Bright pink flower buds opening to white and pink flowers.
5. Long peduncles holding flowers mainly above foliage.

PARENTAL COMPARISON

Plants of the new cultivar 'Harvest Moon' are similar to the female parent in most horticultural characteristics. However, foliage of 'Harvest Moon' is green with a maroon underside. The seed parent has entirely green leaves, which do not turn the distinctive copper color seen on 'Harvest Moon' in the Fall.

The pollen parent cannot be specifically identified.

COMMERCIAL COMPARISON

Plants of the new cultivar 'Harvest Moon' are similar to the commercial variety 'Metallic Mist' U.S. Plant Pat. No. 19,567 in most horticultural characteristics. However, 'Harvest Moon' differs in the following:

1. The new variety has a green leaf with a maroon underside; 'Metallic Mist' foliage is greyed-green on the upper surface and green on the underside.
2. The new variety is more tolerant of heat and humidity than this comparator.
3. The new variety is more root hardy than this comparator.
4. The new variety has a larger leaf size than this comparator.
5. The new variety has a larger flower size
6. Plants of the new variety are larger than this comparator.

Plants of the new cultivar 'Harvest Moon' are similar to the commercial variety 'Fireworks', unpatented, in most horticultural characteristics. However, 'Harvest Moon' differs in the following:

1. The new variety is more root hardy than 'Fireworks'.
2. The new variety has a larger flower size than 'Fireworks'.
3. Plants of the new variety are larger and rounder than plants of 'Fireworks'.
4. The new variety has a green leaf with a maroon underside; 'Fireworks' as a greyed-green leaf with various shades of greyed-purple.

BRIEF DESCRIPTION OF THE PHOTOGRAPHS

The accompanying photograph in FIG. 1 illustrates in full color a typical plant of 'Harvest Moon' grown outdoors in Loxley, Ala. This plant is approximately 1 year old, planted in the ground.

Figure 1:
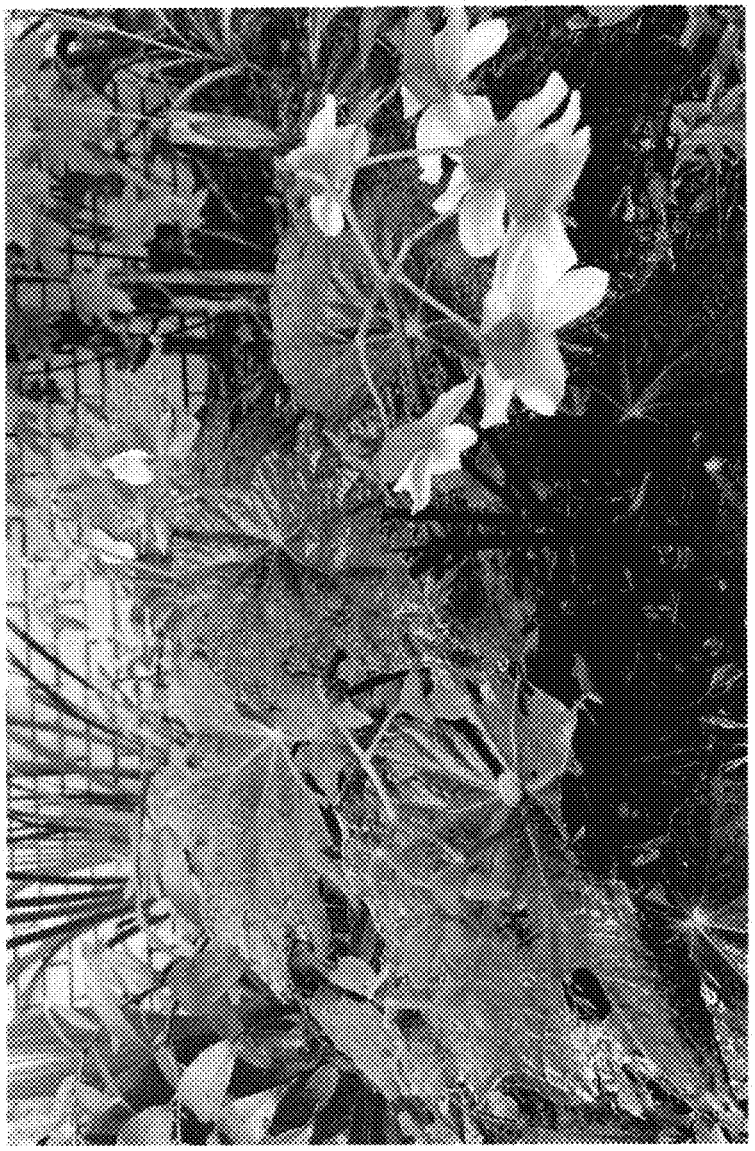
Figure 2:
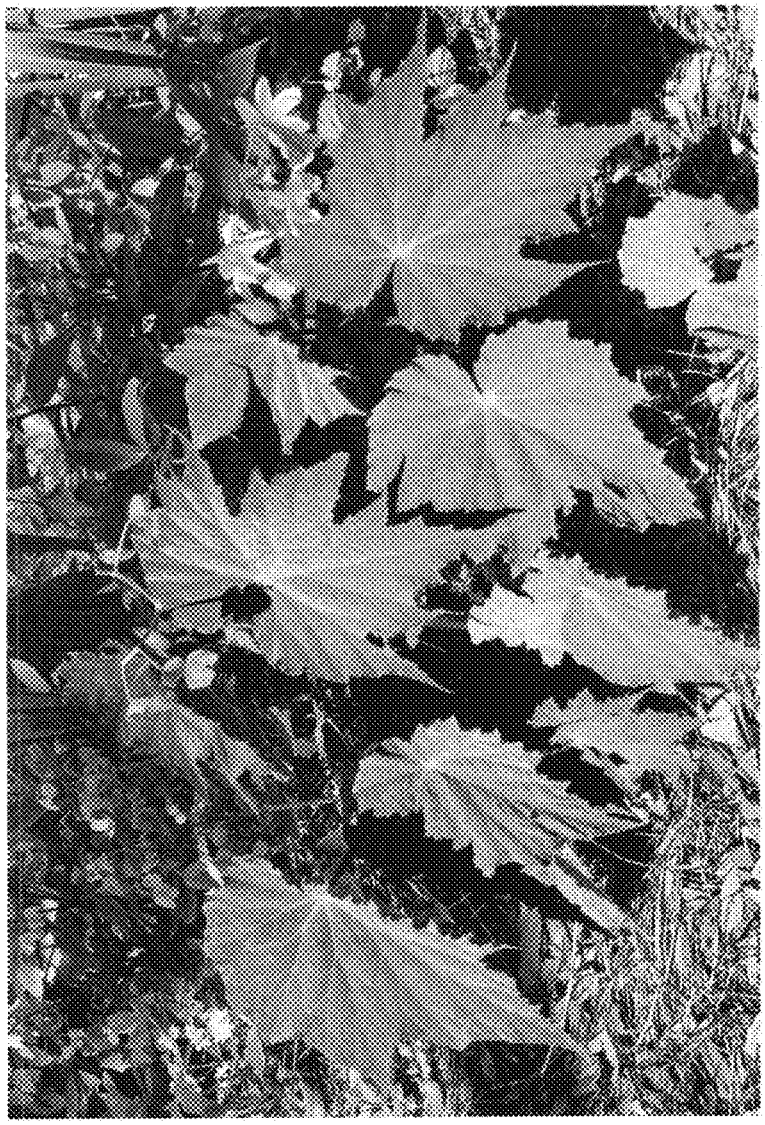
FIG. 2 illustrates the same plant in the Fall, having a coppery coloration to the foliage.
Figure 3:
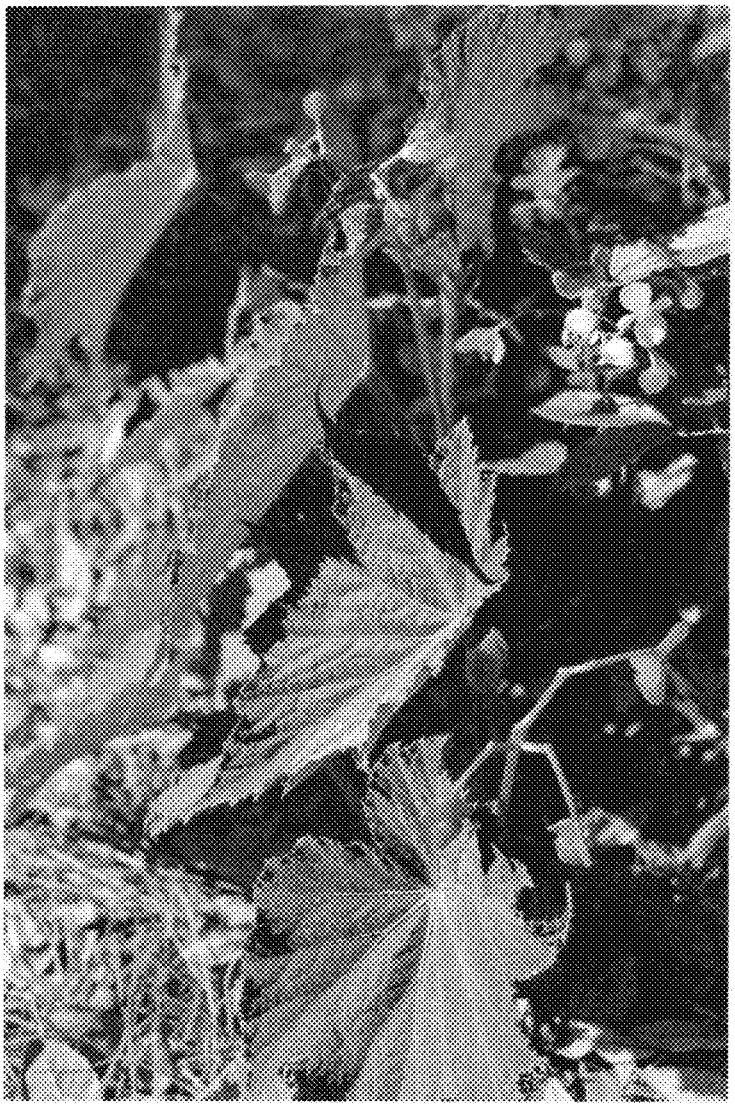
FIG. 3 shows the coloration of the underside of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Harvest Moon' plants grown in outdoors in Loxley, Ala. during Spring. Temperatures ranged from a low temperature about 55° F. at night to a high around 85° C. during the day. No artificial light, photoperiodic treatments or chemical treatments were given to the plants. Measurements and numerical values represent averages of typical plant types.

Botanical classification: *Begonia* hybrid 'Harvest Moon'.

Age of the plant described: Approximately 1 year.

Container size of the plant described: 1-gallon commercial container.

PROPAGATION

Typically reproduced commercially by tissue culture. Leaf cutting propagation is also possible.

PLANT

Growth habit: Upright flowering tender perennial.

Pot size of plant described: 1-gallon.

Height: About 50 cm to 55 cm.

Plant spread: About 45 cm to 60 cm.

Growth rate: Moderate to rapid.

Branching characteristics: Basal branching, breaking into 2 lateral branches at about 10 to 14 cm with maturity.

Quantity of branches: About 10 to 16.

Characteristics of branches:

*Length*.—About 16 cm.

*Form*.—Round in cross section.

*Diameter*.—Approximately 1.0 cm.

*Color*.—Near RHS Greyed-Red 180C.

*Texture*.—Mainly glabrous. Very sparse, irregular hirsute hairs, about 4 mm long colored near White 155C.

*Strength*.—Weak to moderate.

Internode length: About 5 to 7 cm.

FOLIAGE

Arrangement: Emerging basally, with maturity 2 emerging from a branch split.

*Quantity*.—Approximately 20 on a plant of this age.

*Average length*.—Average range 21 to 24 cm.

*Average width*.—Average range 18 to 20 cm.

*Shape of blade*.—Broad kidney shaped.

*Apex*.—Elongated acute.

*Base*.—Cordate.

*Margin*.—5 moderately shallow lobes with very shallow crenation.

*Texture of top surface*.—Glabrous, leathery.

*Texture of bottom surface*.—Glabrous. Very sparse hirsute hairs along main veins.

*Aspect*.—Puckered, overall flat.

*Color*.—Young foliage upper side: Near RHS Green 136A. Young foliage under side: Near RHS Greyed-Orange N172B. Mature foliage upper side: Near RHS Green 137A. Mature foliage under side: Near RHS Greyed-Orange 172C with an overlay N172C. Fall foliage upper side: Near RHS Yellow-Green 144A with overlay Greyed-Orange N167C. Fall foliage under side: Near RHS Greyed-Orange 167A with an overlay Greyed-Orange N167C.

*Venation*.—Type: Palmate. Venation color upper side: Near RHS Green 138B. Fall venation colored near Yellow-Orange 18C, flushed Red 48A near attachment. Venation color under side: Near RHS Greyed-Orange N172A.

*Petiole*.—Length: Average range 15 to 20 cm. Diameter: 7 to 8 mm. Color: Near RHS Yellow-Green 146D heavily flushed Greyed-Purple 183C. Greyed-Purple flush much stronger at base. Texture: Glabrous. Rarely a hirsute hair bout 4 mm long.

*Stipule description*.—1 or 2 per node, non-fleshy, becoming completely dry and papery before leaves fully expand. Length: Approximately 2.5 cm. Diameter: Approximately 1.2 cm. Color: Begins near Greyed-Orange 168C, turning Greyed-Orange 166D when dry. Texture: Glabrous.

FLOWER

Flowering habit: Continuously flowering during Spring and Summer. Flowering begins in May, in the Gulf Coast of the US.

Inflorescence and flower type and habit: Single flowers arranged in axillary cymes. Cymes held slightly above or within foliage, approximately 2 to 4 flowers per cyme.

Cyme size:

*Diameter*.—Approximately 12 cm.

*Height*.—Approximately 5 cm.

Flower longevity on plant: About 10 days, depending upon environmental conditions.

Persistent or self-cleaning: Self-Cleaning.

Bud:

*Shape*.—Ovate.

*Length*.—Approximately 3 cm, including bracts. Tepal bud alone about 1.4 cm.

*Diameter*.—Approximately 1 cm, including bracts. Tepal bud alone about 1.0 cm.

*Color*.—Tepal bud near RHS Red-Purple N57B. Immature bracts around bud colored near Red 55A.

Flower size:
*Diameter*.—Approximately 6.0 cm.
*Depth*.—Approximately 1.5 cm, including protruding stamens.
Tepals:
*Quantity*.—Approximately 5.
*Arrangement*.—Rotate.
*Length*.—Approximately 3 cm.
*Width*.—Approximately 2.1 cm.
*Shape*.—Ovate.
*Apex*.—Obtuse.
*Base*.—Broad attenuate.
*Margin*.—Entire.
*Aspect*.—Slight upward curve.
*Texture, upper and lower surfaces*.—Glabrous
*Appearance, upper and lower surfaces*.—Slightly iridescent.
*Color*.—When opening, upper surface: Near RHS Red 55A flushed Red-Purple N57B. When opening, lower surface: Near RHS Red-Purple N57C. Fully opened, upper surface: Near RHS White 155C streaked Red 55C. Fully opened, lower surface: Near RHS White 155C streaked Red 55C.
Flower bracts
*Quantity per flower*.—2.
*Shape*.—Ovate, strongly concave.
*Length*.—Approximately 2.7 cm.
*Diameter*.—Approximately 1.4 cm, when manually flattened.
*Apex*.—Acute.
*Base*.—Truncate.
*Margin*.—Entire.
*Texture*.—Glabrous.
*Aspect*.—Strongly curved inward towards tepals.
*Color*.—Near RHS Yellow-Green 151B flushed Red 52A when mature. Immature bracts near Red 52A.
Peduncles:
*Length*.—Average 20 cm.
*Diameter*.—Approximately 4 mm.
*Angle*.—About 15° to the lateral branch.
*Strength*.—Moderate, flexible.
*Texture*.—Glabrous.
*Color*.—Near RHS Yellow-Green 151A flushed Greyed-Red 182A. Base near Greyed-Purple 183C.
Pedicels:
*Length*.—Approximately 3.5 cm.
*Diameter*.—Approximately 3 mm.
*Angle*.—About 45° to the lateral branch.
*Strength*.—Moderate, flexible.
*Texture*.—Glabrous.
*Color*.—Near RHS Yellow-Green 151B flushed Red 55A.
Fragrance: None.

REPRODUCTIVE ORGANS

Stamens:
*Number*.—8, arising from staminoidal column.
Anthers:
*Description*.—Fleshy, curly.
*Length*.—Free portion about 7 mm.
*Color*.—Near RHS Green-Yellow 1A.
*Pollen*.—Scant to none. Colored near Red 54D.
Pistil:
*Number*.—1.
*Length*.—Approximately 1.5 cm.
*Style*.—Length: Approximately 2 mm. Color: Near RHS Colored near Red 54D.
*Stigma*.—Shape: Linear. Color: Near RHS Colored near Red 54A. Ovary Color: Near RHS Yellow-Green 145B.

OTHER CHARACTERISTICS

Seeds: Not observed.
Disease/pest resistance: Moderate resistance and susceptibility to common diseases and pests of *Begonia* have been observed in the new variety.
Temperature tolerance: USDA Zone 7-9.

What is claimed is:

1. A new and distinct cultivar of *Begonia* plant named 'Harvest Moon' as herein illustrated and described.

* * * * *